United States Patent [19]
Lilly, Jr.

[11] Patent Number: 5,642,738
[45] Date of Patent: Jul. 1, 1997

[54] ANTI-SNORING DEVICE WITH REDUCIBLE SIZE

[76] Inventor: Frank T. Lilly, Jr., 1024 Leslie La., Azle, Tex. 76020

[21] Appl. No.: 678,230

[22] Filed: Jul. 11, 1996

Related U.S. Application Data

[60] Provisional application No. 60/018,479, May 28, 1996.
[51] Int. Cl.⁶ ............................................. A61F 5/56
[52] U.S. Cl. ............................................. 128/848; 128/859
[58] Field of Search ........................ 128/848, 859–862; 2/2

[56] References Cited

U.S. PATENT DOCUMENTS

| | | |
|---|---|---|
| 746,869 | 12/1903 | Moulton . |
| 1,483,694 | 2/1924 | Stukey . |
| 2,178,128 | 10/1939 | Waite . |
| 2,627,268 | 2/1953 | Leppich . |
| 2,867,212 | 1/1959 | Nunn, Jr. . |
| 3,496,936 | 2/1970 | Gores .................. 128/861 |
| 3,818,906 | 6/1974 | Stubbs .................. 128/860 |
| 4,817,636 | 4/1989 | Woods .................. 428/848 |
| 5,052,410 | 10/1991 | Stubbs .................. 128/859 |
| 5,234,005 | 8/1993 | Kittelsen .................. 128/859 |
| 5,447,168 | 9/1995 | Bancroft .................. 128/861 |

FOREIGN PATENT DOCUMENTS 0312368   4/1989   European Pat. Off. .

*Primary Examiner*—Michael A. Brown
*Attorney, Agent, or Firm*—Richard C. Litman

[57] ABSTRACT

An anti-snoring device inserted between the gums and lips of a user. The device comprises a flexible, elongate oval membrane having a handle located centrally of one side of the membrane to facilitate easy placement into and removal from the mouth. The handle depends from the membrane at a junction of approximately one-quarter inch long, which allows the membrane more uniformly to flex or bend when placed into the mouth of a user. In the same side of the membrane containing the handle, a pair of score grooves are formed at a one-eighth inch intervals from the perimeter of the membrane. A pair of outer score guides, which extend between the perimeter of the membrane and the outer score groove, and a pair of inner score guides, which extend between the inner and outer score grooves, facilitate easy trimming of the device to fit the mouth of any user. The four score guides allow the membrane to be trimmed four times, for a total possible reduction of one-half inch in length and one-half inch in height.

13 Claims, 3 Drawing Sheets

ANTI-SNORING DEVICE WITH REDUCIBLE SIZE

This application is based upon the U.S. Provisional patent application Ser. No. 60/018,479 filed on May 28, 1996.

BACKGROUND OF THE INVENTION

1. Field of the Invention

The present invention relates to a device intended to prevent its user from snoring. More specifically, the present invention relates to an anti-snoring device that is both manipulable and reducible to accommodate different mouth sizes.

2. Description of the Prior Art

To be accused of snoring is enough to keep many persons awake at night wondering whether they are guilty of such deeds. Yet most persons will agree, it is far worse to suffer through a night of broken sleep as a result of another's thundering nocturnal etudes.

It is generally accepted that snoring is the result of breathing through the mouth that causes vibrations of the soft palate against the uvula. In developing devices to assist individuals to overcome their snoring problem, the prior art almost exclusively has attempted to remedy the problem by preventing or restricting the flow of air through the mouth.

U.S. Pat. No. 746,869, which issued to Stillman A. Moulton on Dec. 15, 1903, discloses an anti-snoring device comprised of a membrane having a central aperture and a flap covering the aperture. The Moulton '869 device, when inserted in its normal position, allows a user to exhale through the mouth, but forces a user to inhale through the nose.

U.S. Pat. No. 2,178,128, which issued to Donald H. Waite on Oct. 31, 1939, discloses an anti-snoring device that utilizes a perforated membrane to limit airflow through the mouth. Thus, the Waite '128 device does not restrict airflow to a single direction or otherwise eliminate all airflow through the mouth.

Each of the devices disclosed in U.S. Pat. No. 1,483,694, which issued to Albert F. Stukey on Feb. 12, 1924, U.S. Pat. No. 2,627,268, which issued to Elsa L. Leppich on Feb. 3, 1953, and U.S. Pat. No. 2,867,212, which issued to William A. Nunn, Jr., on Jan. 6, 1959, utilize a solid membrane inserted between the lips and gums to prevent airflow in either direction through the mouth.

U.S. Pat. No. 4,817,636, which issued to Thomas H. Woods on Apr. 4, 1989, also uses a solid membrane to prevent airflow in either direction through the mouth. The device disclosed in Woods '636, however, is adhered in place over the mouth to prevent airflow in either direction through the mouth.

While each of the above described devices may be successful in arresting or otherwise correcting the habit of snoring, none of the devices is easily manipulable by the user. Furthermore, none of the above devices is easily reducible in its height or length to facilitate more comfortable use of the device by persons having variously sized jaws.

None of the above inventions and patents, taken either singly or in combination, is seen to describe the instant invention as claimed.

SUMMARY OF THE INVENTION

The anti-snoring device of the present invention comprises a flexible, elongate oval membrane having a handle on one side of the membrane to facilitate easy placement into and removal from the mouth. On the same side containing the handle are a pair of spaced grooves that extend about the perimeter entire of the membrane. The outer groove lies at a distance of approximately one-eighth inch from the perimeter of the membrane. The inner groove lies at a distance of approximately one-eighth inch inside the outer groove, or one-quarter inch from the perimeter of the membrane. The grooves, which reach a depth of approximately half the thickness of the membrane, allow a user to reduce the height and length of the membrane by trimming away a portion of its perimeter.

To provide a simple and clean trimming of the device, two score guides are provided at each of two diagonally situated corners. The outer score guides extend between the perimeter and the outer groove, whereas the inner score guides extend between the outer groove and inner groove. Like the inner and outer grooves, the guide marks reach a depth of approximately half the thickness of the membrane.

Because the grooves are spaced as described above, a user may trim the device a total of four times, in approximately one-eighth inch intervals, for a maximum length and height reduction of one-half inch.

Accordingly, it is a principal object of the invention to provide an effective anti-snoring device that is capable of being reduced in height and length to accommodate a variety of users who may have different mouth sizes.

It is another object of the invention to provide an effective anti-snoring device that is flexible and comfortable to wear.

It is a further object of the invention to provide an effective anti-snoring device that a user may easily manipulate while inserting or removing the device from the mouth.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
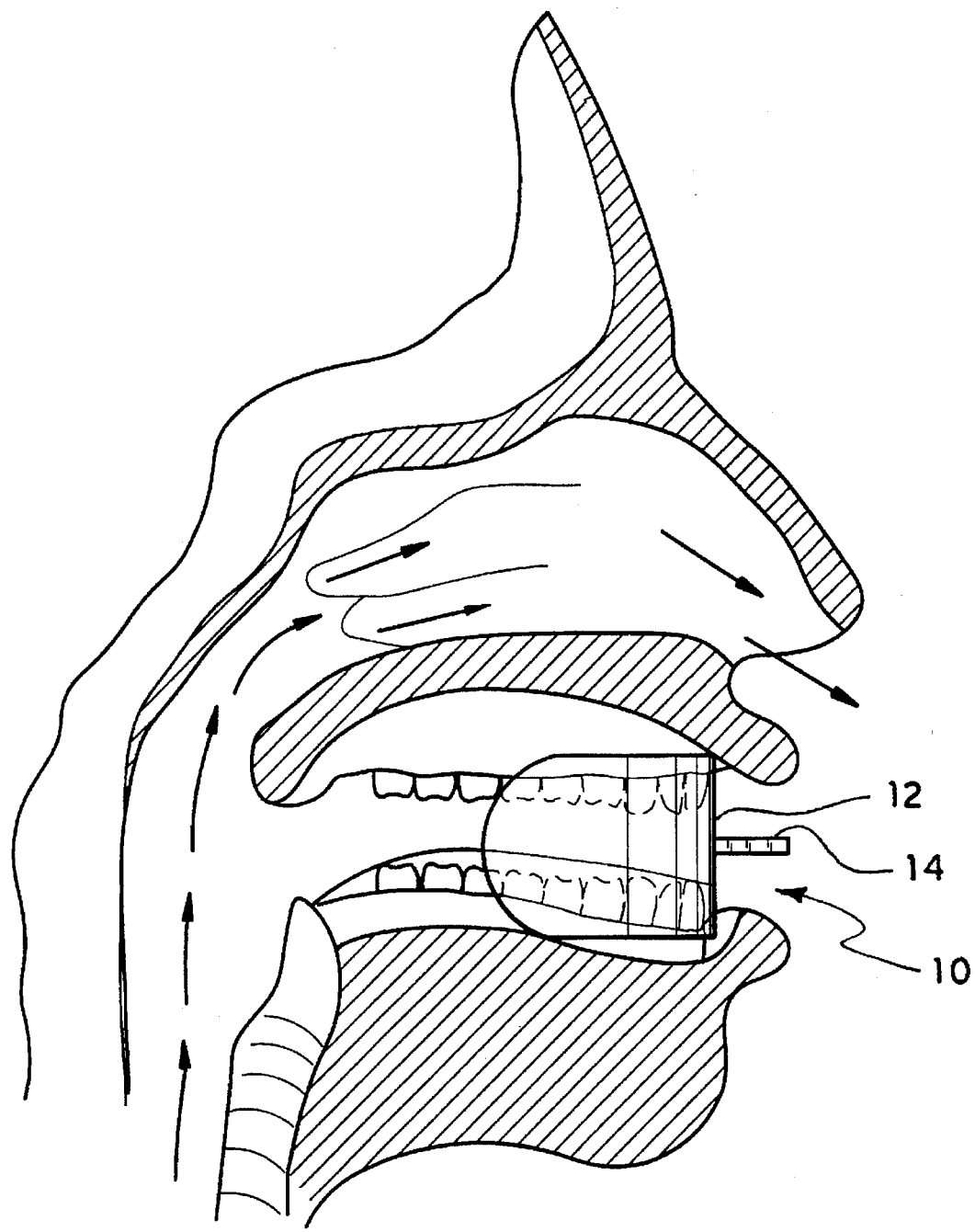
FIG. 1 is an environmental view of the device, at its fully reduced size, fitted for use in a person's mouth, with a portion of the person's face broken away to expose the interior of the mouth and air passages through the nose and sinuses.
Figure 2:
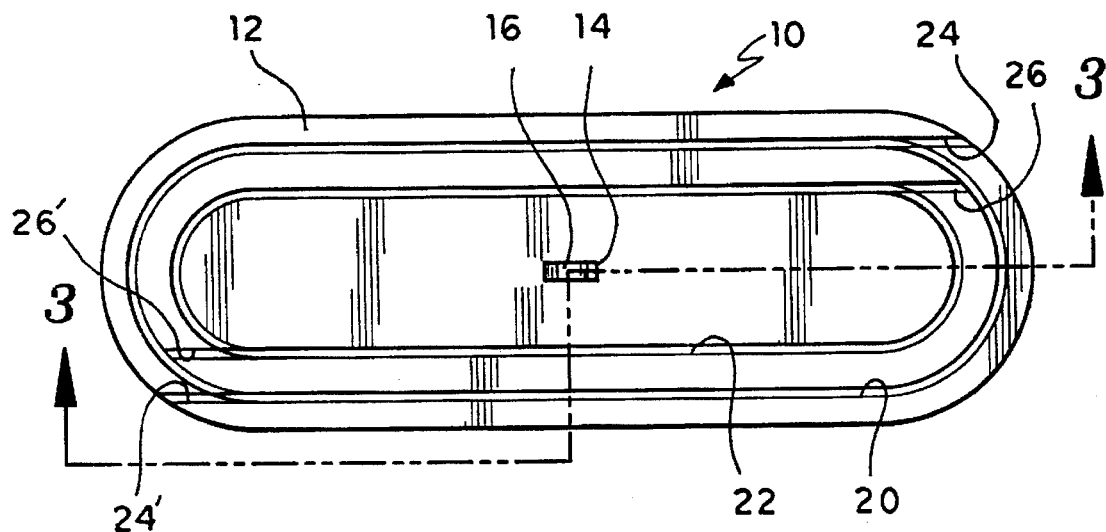
FIG. 2 is a plan view of the present invention.

Referring now to the figures by numerals of reference, and first to FIG. 1, 10 denotes generally an anti-snoring device of the present invention, which I prefer to call the Snore Stopper. The anti-snoring device 10 is formed of a thermoplastic material that is both lightweight and flexible, or any other suitable material having similar properties. The anti-snoring device 10 of the present invention has a unitary structure comprising an elongate oval membrane 12 and a centrally located handle 14 projecting outwardly approximately one-half inch from one side of membrane 12.

Figure 3:
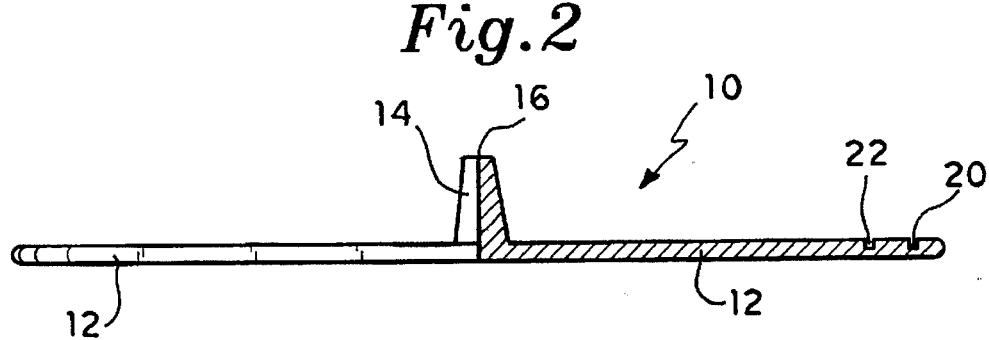
FIG. 3 is a side, partly elevational, partly sectional view taken along lines 3—3 of FIG. 2.
Figure 4:
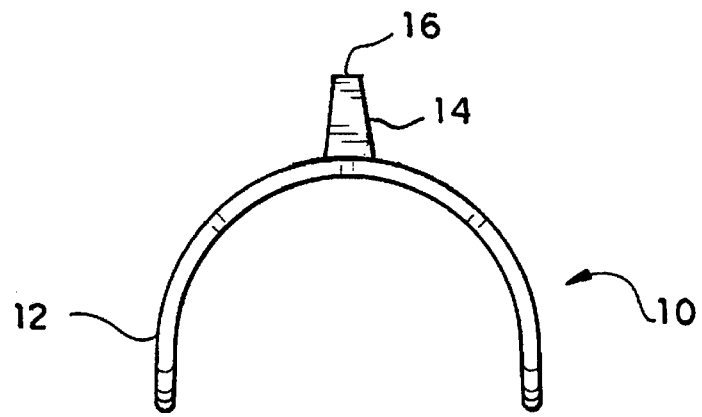
FIG. 4 is a side elevational view of the device shown in its bent form as during use.

Handle 14 perpendicularly depends from membrane 12 with its sides tapering to a truncated end 16, which gives the handle a generally trapezoidal appearance as shown in FIGS. 3 and 4. Because handle 14 is relatively small, i.e., approximately one-quarter inch long at its junction with membrane 12, the handle facilitates a more uniform bending of membrane 12 during use. This allows membrane 12 adequately to conform to a user's mouth, which ensures a more comfortable fit of anti-snoring device 10. It should be noted, however, that any handle having a relatively short junction with membrane 12 also would suffice because such a handle would provide for a manipulable anti-snoring device 10 having a flexible membrane 12.

On the same side as handle 14, membrane 12 contains outer and inner score grooves 20 and 22, respectively, in spaced relation to the entire perimeter of membrane 12. The outer score groove 20 lies at a distance of approximately one-eighth inch from the perimeter. The inner score groove 22 lies at a distance of approximately one-eighth inch inside the outer score groove 20, or one-quarter inch from the perimeter. The score grooves 20 and 22, which reach a depth of approximately half the thickness of the membrane 12, allow a user to reduce the height and length of the device 10 by trimming away a portion of the membrane. In addition, score grooves 20 and 22 contribute to increased flexibility of the membrane 12, which lends itself to an anti-snoring device 10 that more comfortably fits in the mouth and better seals between the lips and gums to prevent airflow.

To provide a simple and clean trimming of the membrane 12, four score guides 24, 24', 26 and 26' are provided. Score guides 24 and 26 are located at one end of membrane 12, and score guides 24' and 26' are located at the opposite end, whereby the two sets are in diagonally opposed relation. The outer score guides 24 and 24' communicate between the perimeter and the outer score groove 20 by extending the straight portions of score groove 20 linearly outwardly to the arcuate perimeter of membrane 12. The inner score guides 26 and 26' communicate between the outer score groove 20 and inner score groove 22, extending the straight portion of score groove 22 linearly outwardly toward the arcuate portions of score groove 20. Like the outer and inner score grooves 20 and 22, respectively, the score guides 24, 24', 26 and 26' reach a depth of approximately half the thickness of the membrane 12.

Because the score grooves 20 and 22 are spaced as described above, a user may reduce the size of the anti-snoring device 10 a total of four times. Each reduction occurs in approximately one-eighth inch intervals, for a maximum length and height reduction of one-half inch.

Figure 5:
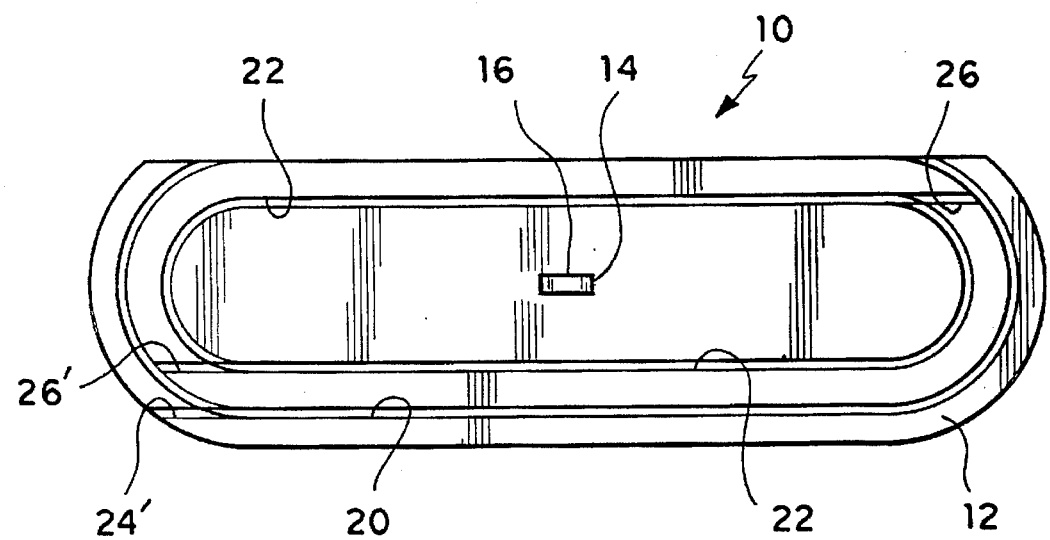
FIG. 5 is a plan view of the device following a first reduction in the size of the membrane.
Figure 6:
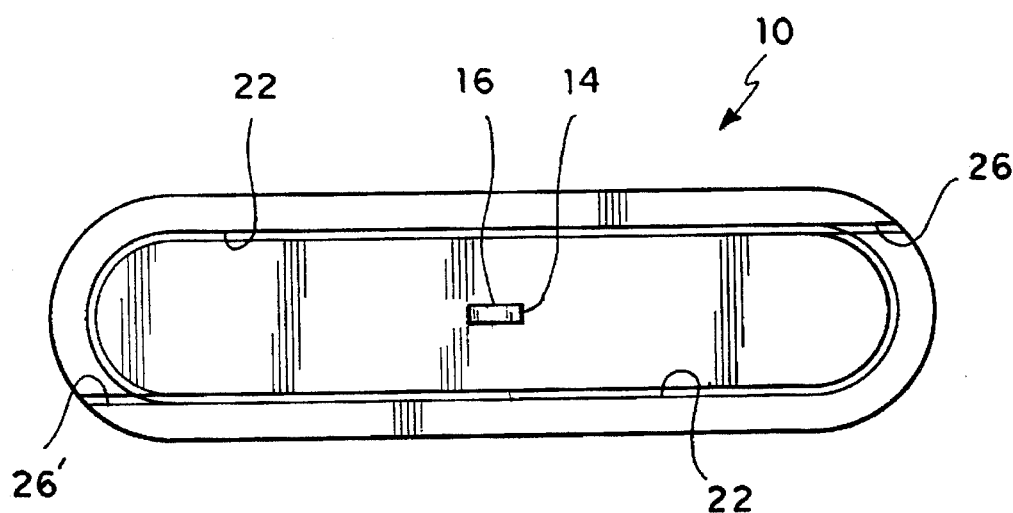
FIG. 6 is a plan view of the device following a second reduction in the size of the membrane.

To effect a first one-eighth inch reduction in the height of the membrane 12, a user will begin cutting at either guide mark 24 or 24', and continue cutting in a straight line until a one-eighth inch strip is removed from one edge of membrane 12, as shown in FIG. 5. To effect a second one-eighth reduction in the height of membrane 12 and a one-quarter inch reduction in the length of membrane 12, the user will cut along the remainder of score groove 20 until the entire outer one-eighth strip is removed from membrane 12, as shown in FIG. 6. To further reduce the height and length of membrane 12, a user may duplicate the above-described operation beginning at guide mark 26 or 26'.

To insert anti-snoring device 10 into the mouth, a user grasps the handle 14 and first urges one end of membrane 12 between the lips and gums, followed by the other end. Once the user positions anti-snoring device 10 between the lips and gums, the user may center the device 10 by manipulating handle 14 thereof. Once the device is centered, the user needs only to relax and breath comfortably through the nasal passages, the process of exhaling being indicated by the arrows in FIG. 1.

While the structure of the anti-snoring device 10 will remain the same for all embodiments thereof, it should be noted that a flavoring, such as peppermint or spearmint, may be mixed into the thermoplastic prior to forming the device 10. Furthermore, a pigment also may be added to produce differently colored devices 10 so as to avoid confusion and facilitate easier identification of an individual's anti-snoring device 10.

It is to be understood that the present invention is not limited to the sole embodiment described above, but encompasses any and all embodiments within the scope of the following claims.

I claim:

1. An anti-snoring device for insertion between the lips and gums, comprising:

a flexible, elongate membrane having a perimeter, a generally uniform thickness and opposed faces;

a handle integral with said membrane, said handle being located centrally of one of said faces of said membrane to allow said membrane to flex along the entire length thereof; and a first score groove in one of said faces of said membrane, said first score groove being in parallel relation with the entirety of the perimeter of said membrane.

2. The anti-snoring device according to claim 1, further comprising:

a second score groove in the same face as said first score groove, said second score groove being in parallel relation with the entirety of the perimeter of said membrane.

3. The anti-snoring device according to claim 2, wherein said first score groove uniformly is located one-eighth inch from the perimeter of said membrane, and said second score groove uniformly is located one-quarter inch from the perimeter of said membrane.

4. The anti-snoring device according to claim 2, further comprising:

first and second score guides extending between the perimeter of said membrane and said first score groove; and third and fourth score guides extending between said first score groove and said second score groove.

5. The anti-snoring device according to claim 4, wherein said membrane is shaped as an elongate oval having parallel opposed linear sides and opposed arcuate ends, and each of said first and second score grooves is characterized by spaced linear portions connected together by opposed arcuate portions;

said first and second score guides co-linearly extending said linear portions of said first score groove outwardly toward the perimeter of said membrane at said arcuate ends thereof; and said third and fourth score guides co-linearly extending said linear portions of said second score groove outwardly toward said arcuate portions of said first score groove.

6. The anti-snoring device according to claim 4, wherein said first score guide and said third score guide are located at one end of said membrane, and said second score guide and said fourth score guide are located at the other end of said membrane.

7. An anti-snoring device for insertion between the lips and gums, comprising:

a flexible, elongate membrane having a perimeter, a generally uniform thickness and opposed faces;

a handle integral with said membrane, said handle being located centrally of one of said faces of said membrane to allow said membrane to flex along the entire length thereof; and guide means on one of said faces of said membrane, said guide means being in parallel relation with the entirety of the perimeter of said membrane, and said guide means providing assistance in the trimming of said membrane to reduce the size of said membrane.

8. The anti-snoring device according to claim 7, wherein said guide means comprises a first score groove in one of said faces of said membrane.

9. The anti-snoring device according to claim 8, wherein said guide means further comprises a second score groove in the same face as said first score groove.

10. The anti-snoring device according to claim 9, wherein said first score groove uniformly is located one-eighth inch from the perimeter of said membrane, and said second score groove uniformly is located one-quarter inch from the perimeter of said membrane.

11. The anti-snoring device according to claim 9, wherein said guide means further comprises:

first and second score guides extending between the perimeter of said membrane and said first score groove;

third and fourth score guides extending between said first score groove and said second score groove.

12. The anti-snoring device according to claim 11, wherein said membrane is shaped as an elongate oval having parallel opposed linear sides and opposed arcuate ends, and each of said first and second score grooves is characterized by spaced linear portions connected together by opposed arcuate portions, said first and second score guides co-linearly extending said linear portions of said first score groove outwardly toward the perimeter of said membrane at said arcuate ends thereof, and said third and fourth score guides co-linearly extending said linear portions of said second score groove outwardly toward said arcuate portions of said first score groove.

13. The anti-snoring device according to claim 11, wherein said first score guide and said third score guide are located at one end of said membrane, and said second score guide and said fourth score guide are located at the other end of said membrane.

* * * * *